US008062367B2

(12) United States Patent
Kirschman

(10) Patent No.: US 8,062,367 B2
(45) Date of Patent: Nov. 22, 2011

(54) SCREW LOCKING MECHANISM AND METHOD

(75) Inventor: David Louis Kirschman, Dayton, OH (US)

(73) Assignee: X-spine Systems, Inc., Miamisburg, OH (US)

( * ) Notice: Subject to any disclaimer, the term of this patent is extended or adjusted under 35 U.S.C. 154(b) by 1109 days.

(21) Appl. No.: 11/622,487

(22) Filed: Jan. 12, 2007

(65) Prior Publication Data

US 2007/0123885 A1    May 31, 2007

Related U.S. Application Data

(63) Continuation-in-part of application No. 11/858,629, filed on Jun. 2, 2004, now Pat. No. 7,641,701, which is a continuation-in-part of application No. 10/675,361, filed on Sep. 30, 2003, now Pat. No. 7,182,782.

(51) Int. Cl.
 A61B 17/80 (2006.01)
 A61B 17/56 (2006.01)
 A61B 17/58 (2006.01)
(52) U.S. Cl. ........ 623/17.11; 606/70; 606/280; 606/289
(58) Field of Classification Search ............... 606/70–71, 606/280–299; 623/17.11–17.16
 See application file for complete search history.

(56) References Cited

U.S. PATENT DOCUMENTS

| | | | |
|---|---|---|---|
| 1,025,008 A | 4/1912 | Miner | |
| 2,677,369 A | 5/1954 | Knowles | |
| 3,848,601 A | 11/1974 | Ma et al. | |
| 3,867,728 A | 2/1975 | Stubstad et al. | |
| 4,157,715 A | 6/1979 | Westerhoff | |
| 4,309,777 A | 1/1982 | Patil | |
| 4,349,921 A | 9/1982 | Kuntz | |
| 4,488,543 A | 12/1984 | Tornier | |
| 4,553,273 A | 11/1985 | Wu | |
| 4,599,086 A | 7/1986 | Doty | |
| 4,611,581 A | 9/1986 | Steffee | |
| 4,696,290 A | 9/1987 | Steffee | |
| 4,714,469 A | 12/1987 | Kenna | |
| 4,743,256 A | 5/1988 | Brantigan | |
| 4,759,766 A | 7/1988 | Buettner-Janz et al. | |
| 4,834,757 A | 5/1989 | Brantigan | |
| 4,878,915 A | 11/1989 | Brantigan | |
| 4,988,349 A | 1/1991 | Pennig | |
| 4,997,432 A | 3/1991 | Keller | |
| 5,041,113 A | 8/1991 | Biedermann et al. | |
| 5,084,049 A | 1/1992 | Asher et al. | |
| 5,085,660 A | 2/1992 | Lin | |
| 5,192,327 A | 3/1993 | Brantigan | |
| 5,246,443 A | 9/1993 | Mai | |

(Continued)

FOREIGN PATENT DOCUMENTS

CA    1292596    12/1991

(Continued)

Primary Examiner — Thomas C. Barrett
Assistant Examiner — Matthew Lawson
(74) Attorney, Agent, or Firm — Jacox, Meckstroth & Jenkins

(57) ABSTRACT

This invention relates to a bony fixation system and method for use as a prosthetic implant. The system and method includes a plate dimensioned to be situated between adjacent bony structures, such as adjacent vertebrae. Screws are provided in one embodiment and are dimensioned or configured to be inserted into a bony structure and to lock against each other to retain the screws and consequently secure the plate in place against the bony structure.

9 Claims, 6 Drawing Sheets

U.S. PATENT DOCUMENTS

| | | |
|---|---|---|
| 5,261,911 A | 11/1993 | Carl |
| 5,290,312 A | 3/1994 | Kojimoto et al. |
| 5,324,290 A | 6/1994 | Zdeblick et al. |
| 5,330,473 A | 7/1994 | Howland |
| 5,364,399 A | 11/1994 | Lowery et al. |
| 5,405,391 A | 4/1995 | Hednerson et al. |
| 5,425,772 A | 6/1995 | Brantigan |
| 5,439,463 A | 8/1995 | Lin |
| 5,549,612 A | 8/1996 | Yapp et al. |
| 5,554,191 A | 9/1996 | Lahille et al. |
| 5,601,551 A | 2/1997 | Taylor et al. |
| 5,601,553 A | 2/1997 | Trebing et al. |
| 5,616,142 A | 4/1997 | Yuan et al. |
| 5,616,144 A | 4/1997 | Yapp et al. |
| 5,620,443 A | 4/1997 | Gertzbein et al. |
| 5,672,177 A | 9/1997 | Seldin |
| 5,681,310 A | 10/1997 | Yuan et al. |
| 5,681,311 A | 10/1997 | Foley et al. |
| 5,702,395 A | 12/1997 | Hopf |
| 5,713,899 A | 2/1998 | Marnay et al. |
| 5,713,900 A | 2/1998 | Benzel et al. |
| 5,716,415 A | 2/1998 | Steffee |
| 5,720,746 A | 2/1998 | Soubeiran |
| 5,776,196 A | 7/1998 | Matsuzaki et al. |
| 5,843,082 A | 12/1998 | Yuan et al. |
| 5,876,402 A | 3/1999 | Errico et al. |
| 5,888,228 A | 3/1999 | Knothe et al. |
| 5,904,683 A | 5/1999 | Pohndorf et al. |
| 5,925,047 A | 7/1999 | Errico et al. |
| 5,951,558 A | 9/1999 | Fiz |
| 5,954,722 A | 9/1999 | Bono |
| 6,030,389 A | 2/2000 | Wagner et al. |
| 6,066,175 A | 5/2000 | Henderson et al. |
| 6,106,557 A | 8/2000 | Robioneck et al. |
| 6,136,002 A | 10/2000 | Shih et al. |
| 6,139,550 A * | 10/2000 | Michelson .................. 606/70 |
| 6,152,927 A * | 11/2000 | Farris et al. .................. 606/287 |
| 6,159,211 A | 12/2000 | Boriani et al. |
| 6,159,213 A | 12/2000 | Rogozinski |
| 6,159,245 A | 12/2000 | Meriwether et al. |
| 6,171,307 B1 | 1/2001 | Orlich |
| 6,193,721 B1 | 2/2001 | Michelson |
| D440,311 S | 4/2001 | Michelson |
| 6,224,602 B1 | 5/2001 | Hayes |
| 6,235,033 B1 | 5/2001 | Brace et al. |
| 6,235,034 B1 | 5/2001 | Bray |
| 6,235,059 B1 | 5/2001 | Benezech et al. |
| 6,245,108 B1 | 6/2001 | Biscup |
| 6,258,089 B1 | 7/2001 | Campbell et al. |
| 6,261,291 B1 | 7/2001 | Talaber et al. |
| 6,261,586 B1 | 7/2001 | McKay |
| 6,264,655 B1 | 7/2001 | Pisharodi |
| 6,293,949 B1 | 9/2001 | Justis et al. |
| D449,692 S | 10/2001 | Michelson |
| 6,306,136 B1 | 10/2001 | Baccelli |
| 6,306,139 B1 | 10/2001 | Fuentes |
| 6,328,738 B1 | 12/2001 | Suddaby |
| 6,361,537 B1 | 3/2002 | Anderson |
| 6,368,351 B1 | 4/2002 | Glenn et al. |
| 6,383,186 B1 | 5/2002 | Michelson |
| 6,398,783 B1 | 6/2002 | Michelson |
| 6,413,259 B1 | 7/2002 | Lyons et al. |
| 6,416,528 B1 | 7/2002 | Michelson |
| 6,428,542 B1 | 8/2002 | Michelson |
| 6,432,106 B1 | 8/2002 | Fraser |
| 6,454,769 B2 | 9/2002 | Wagner et al. |
| 6,454,771 B1 | 9/2002 | Michelson |
| 6,485,517 B1 | 11/2002 | Michelson |
| 6,503,250 B2 | 1/2003 | Paul |
| 6,527,776 B1 | 3/2003 | Michelson |
| 6,533,786 B1 | 3/2003 | Needham et al. |
| 6,558,423 B1 | 5/2003 | Michelson |
| 6,558,424 B2 | 5/2003 | Thalgott |
| 6,569,201 B2 | 5/2003 | Moumene et al. |
| 6,575,975 B2 | 6/2003 | Brace et al. |
| 6,592,586 B1 | 7/2003 | Michelson |
| 6,599,290 B2 | 7/2003 | Bailey et al. |
| 6,602,256 B1 | 8/2003 | Hayes |
| 6,602,257 B1 | 8/2003 | Thramann |
| 6,605,090 B1 | 8/2003 | Trieu et al. |
| 6,613,053 B1 | 9/2003 | Collins et al. |
| 6,616,666 B1 | 9/2003 | Michelson |
| 6,620,163 B1 | 9/2003 | Michelson |
| 6,626,907 B2 | 9/2003 | Blain et al. |
| 6,652,525 B1 | 11/2003 | Assaker et al. |
| 6,669,700 B1 | 12/2003 | Farris et al. |
| 6,676,703 B2 | 1/2004 | Biscup |
| 6,679,883 B2 | 1/2004 | Hawkes et al. |
| 6,699,249 B2 | 3/2004 | Schlapfer et al. |
| 6,712,818 B1 | 3/2004 | Michelson |
| 6,755,833 B1 | 6/2004 | Paul et al. |
| 6,776,798 B2 | 8/2004 | Camino et al. |
| 6,837,905 B1 | 1/2005 | Lieberman |
| 6,890,334 B2 | 5/2005 | Brace et al. |
| 6,916,320 B2 | 7/2005 | Michelson |
| 6,926,737 B2 | 8/2005 | Jackson |
| 6,936,050 B2 | 8/2005 | Michelson |
| 6,936,051 B2 | 8/2005 | Michelson |
| 6,964,664 B2 | 11/2005 | Freid et al. |
| 6,969,390 B2 | 11/2005 | Michelson |
| 7,001,387 B2 | 2/2006 | Farris et al. |
| 7,033,394 B2 | 4/2006 | Michelson |
| 7,041,105 B2 | 5/2006 | Michelson |
| 7,041,135 B2 | 5/2006 | Michelson |
| 7,044,952 B2 | 5/2006 | Michelson |
| 2002/0045898 A1 | 4/2002 | Freid et al. |
| 2002/0058939 A1 | 5/2002 | Wagner et al. |
| 2002/0120273 A1 | 8/2002 | Needham et al. |
| 2002/0143400 A1 | 10/2002 | Biscup |
| 2002/0173790 A1 | 11/2002 | Chang et al. |
| 2002/0183755 A1 | 12/2002 | Michelson |
| 2002/0183756 A1 | 12/2002 | Michelson |
| 2002/0183757 A1 | 12/2002 | Michelson |
| 2002/0188296 A1 | 12/2002 | Michelson |
| 2003/0018335 A1 | 1/2003 | Michelson |
| 2003/0023307 A1 | 1/2003 | Michelson |
| 2003/0045880 A1 | 3/2003 | Michelson |
| 2003/0060828 A1 | 3/2003 | Michelson |
| 2003/0078668 A1 | 4/2003 | Michelson |
| 2003/0093082 A1 | 5/2003 | Campbell et al. |
| 2003/0105462 A1 | 6/2003 | Haider |
| 2003/0181912 A1 | 9/2003 | Michelson |
| 2003/0187443 A1 | 10/2003 | Lauryssen et al. |
| 2003/0191471 A1 | 10/2003 | Michelson |
| 2003/0191472 A1 | 10/2003 | Michelson |
| 2003/0199876 A1 | 10/2003 | Brace et al. |
| 2003/0199983 A1 | 10/2003 | Michelson |
| 2003/0208204 A1 | 11/2003 | Bailey et al. |
| 2003/0225409 A1 | 12/2003 | Freid et al. |
| 2004/0019353 A1 | 1/2004 | Freid et al. |
| 2004/0030338 A1 | 2/2004 | Paul |
| 2004/0092939 A1 | 5/2004 | Freid et al. |
| 2004/0097934 A1 | 5/2004 | Farris et al. |
| 2004/0122426 A1 | 6/2004 | Michelson |
| 2004/0127897 A1 | 7/2004 | Freid et al. |
| 2004/0127903 A1 | 7/2004 | Schlapfer et al. |
| 2004/0133205 A1 | 7/2004 | Thramann et al. |
| 2004/0181226 A1 | 9/2004 | Michelson |
| 2004/0181229 A1 | 9/2004 | Michelson |
| 2004/0186476 A1 | 9/2004 | Michelson |
| 2004/0193269 A1 | 9/2004 | Fraser et al. |
| 2004/0193270 A1 | 9/2004 | DiMauro et al. |
| 2004/0193271 A1 | 9/2004 | Fraser et al. |
| 2004/0199254 A1 | 10/2004 | Louis et al. |
| 2004/0210313 A1 | 10/2004 | Michelson |
| 2004/0230309 A1 | 11/2004 | DiMauro et al. |
| 2005/0038513 A1 | 2/2005 | Michelson |

FOREIGN PATENT DOCUMENTS

| | | |
|---|---|---|
| CA | 2133276 | 4/1995 |
| CA | 2163243 A1 | 9/1995 |
| CA | 2383634 A1 | 8/2001 |
| DE | 4409833 A1 | 10/1995 |
| EP | 0179695 A1 | 4/1986 |
| EP | 0307241 A2 | 3/1989 |
| EP | 599640 A1 | 6/1994 |
| EP | 1169971 A2 | 1/2002 |

| | | | |
|---|---|---|---|
| EP | 1437105 A1 | 7/2004 |
| FR | 2727005 A1 | 5/1996 |
| FR | 2827150 A1 | 1/2003 |
| WO | 89/09035 A1 | 10/1989 |
| WO | 97/20526 A1 | 6/1997 |

| | | |
|---|---|---|
| WO | 99/63914 A1 | 12/1999 |
| WO | 00/66044 A1 | 11/2000 |
| WO | 00/66045 A1 | 11/2000 |
| WO | 03005939 A2 | 1/2003 |

* cited by examiner

SCREW LOCKING MECHANISM AND METHOD

RELATED APPLICATION DATA

This application is a continuation-in-part of U.S. patent application Ser. No. 10/858,629, filed Jun. 2, 2004, which is a continuation-in-part of U.S. patent application Ser. No. 10/675,361 filed Sep. 30, 2003.

FIELD OF THE INVENTION

The present invention relates to orthopedic implants and to methods of treating bony defects, and more particularly to plate systems used for fusing bony structures.

BACKGROUND

The spine of most human adults consists of 24 connected bones called vertebrae. The cervical vertebrae begin at the base of the skull. Seven vertebrae make up the cervical spine, which are abbreviated C1, C2, C3, C4, C5, C6 and C7. The cervical vertebrae are smaller in size compared to other spinal vertebrae. The purpose of the cervical spine is to contain and protect the spinal cord, support the skull, and enable a wide range of head movement. The vertebrae allow the head to rotate side to side, bend forward and backward.

Frequently cervical spine disorders require surgery to relieve painful symptoms. One of the contributing factors associated with most spine disorders is the dehydration of the intervertebral disks, which act as a cushion between adjacent vertebrae. Over time these disks can dry out and become flattened, causing the vertebrae to lose height and its healthy resilience. The degeneration of the disks allow the vertebrae get closer together and cause nerve irritation, which usually stems from a ruptured disc, bone spurs or stenosis. Vertebral motion (neck movement) results in chronic pain.

Cervical fusion has become an accepted procedure to relieve the pressure on one or more nerve roots, or on the spinal cord. It involves the stabilization of two or more vertebrae by locking (fusing) them together in a desired spacing and orientation. The fusion restores the proper distance between the vertebrae thus preventing nerve irritation.

The cervical spine may be approached by the surgeon anteriorly, which refers to the front. The surgeon reaches the cervical spine through a small incision in the front of the neck. After retracting neck muscles, the surgeon often removes the affected intervertebral disk, which takes the pressure off the nerves or spinal cord. This is procedure is known as decompression. The surgeon then replaces the removed disk with a bone graft which aids in the fusion of adjacent vertebrae and restores the distance between the vertebrae. The surgeon then may use various types of plates which provide extra pressure and support the neck to make certain that the bones fuse adequately. Holes may be drilled or tapped in the bone to allow for attachment of a plate using a bone screw or other fastener.

One of the problems associated with the fusion of cervical vertebrae is the tendency of the screws or other fasteners to loosen over time. As the fasteners or screws loosen the plate is not able to support or maintain the proper orientation of the vertebrae. The plate and other associated implants, which are no longer secure, can cause irritation and even trauma to local tissue structures.

What is needed, therefore, is a system and method, which facilitates overcoming one or more of the aforementioned problems as well as other problems and to provide a device that has unique features that will facilitate reducing the risk associated with neurological surgeries and advance the present state of the art.

SUMMARY OF THE INVENTION

In one aspect, this invention comprises a plate system for stabilizing various bony structures, said plate system comprising a first screw having a first head, said first head comprising a wall having a first portion and a second portion; and a second screw having a second head having a second wall; said first portion being dimensioned such that when said first portion is situated opposite said second wall, said second head may be rotated to screw said second screw into said spinal bone of said spinal column, said first portion of said first screw may thereafter be rotated so that said second portion may engage said second wall in order to facilitate retaining said first and second screws in a tightened position.

In yet another aspect, this invention comprises a method for fastening a plate to a bony structure comprising the steps of: situating the plate in proximity to the spinal column; positioning a first screw through an aperture in the plate; screwing said first screw into a spinal bone in the spinal column; positioning a second screw through the plate; screwing a second screw into the spinal bone until it becomes tightened; and tightening said first screw until a portion of a head of the first screw engages a head of the second screw to retain the first and second screws in a tightened position.

DETAILED DESCRIPTION

Figure 1:
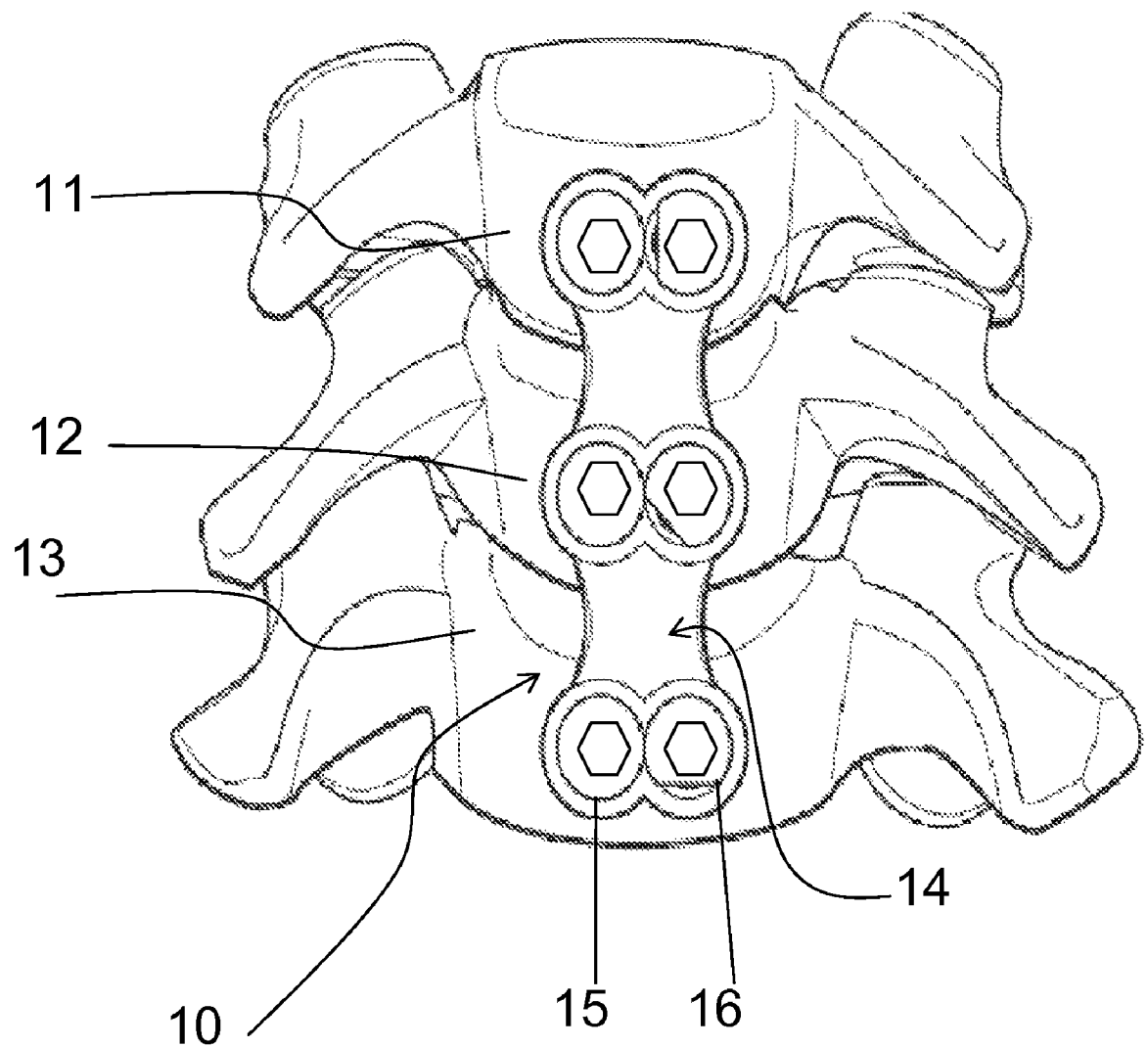
FIG. 1 is a anterior view of a human spine illustrating one embodiment of a locking plate system implanted to a bony structure.

Referring to FIG. 1, in one embodiment, a plate system 10 is illustrated for stabilizing or fusing various bony structures, such a vertebrae of a human spine 11-13. The plate system 10 includes a plate 14 and at least two bone anchors 15 and 16, such as bone screws. In order to securely fasten the plate 14 to various bony structures, such a vertebrae of a human spine 11-13, a locking system, means and method are provided for retaining the bone anchors 15 and 16 to the plate 14. The details of the locking system, means and method which are later described in further detail.

Figure 2:
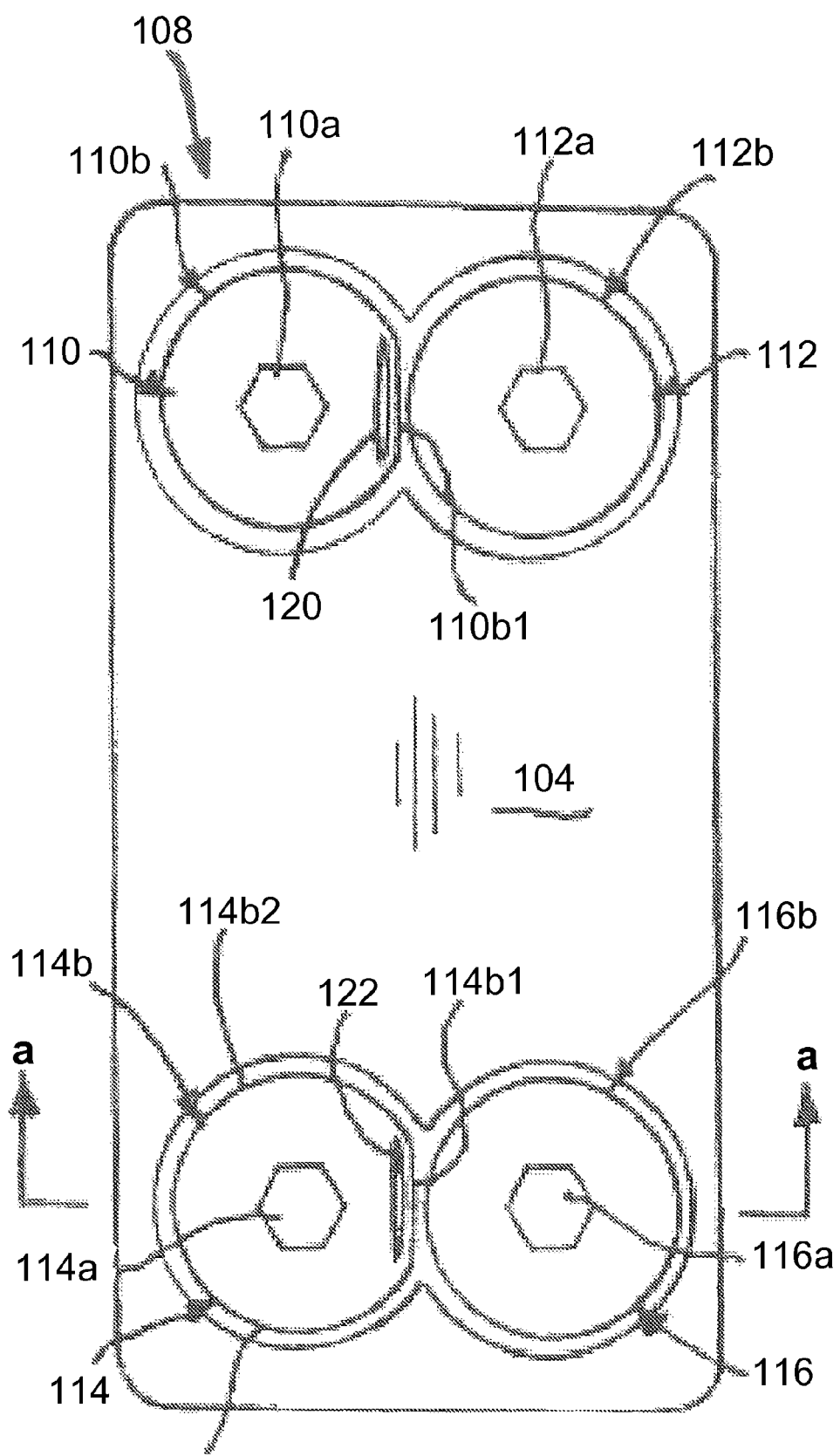
FIG. 2 is a view of another embodiment of the invention showing the plurality of fasteners or screws in an unlocked position.

FIG. 2 illustrates another embodiment of a plate system 108. The plate system 108 includes a plate 104 and at least two bone anchors 110 and 112. In order to securely fasten the plate 104 to various bony structures, such a vertebrae of a human spine (not shown), a locking system, means and method are provided for retaining the bone anchors 110 and 112 to the plate 104.

The plate system 108 comprises a plurality of screws, fastening means or fasteners 110, 112, 114 and 116 that are received in openings, such as openings 118 (FIG. 4) in the plate 104 as shown. Note that the fasteners 110-116 comprise a plurality of female openings or slots 110a, 112a, 114a and 116a for receiving a tool, such as a hex wrench for tightening and loosening the fasteners 110-116.

Figure 4:
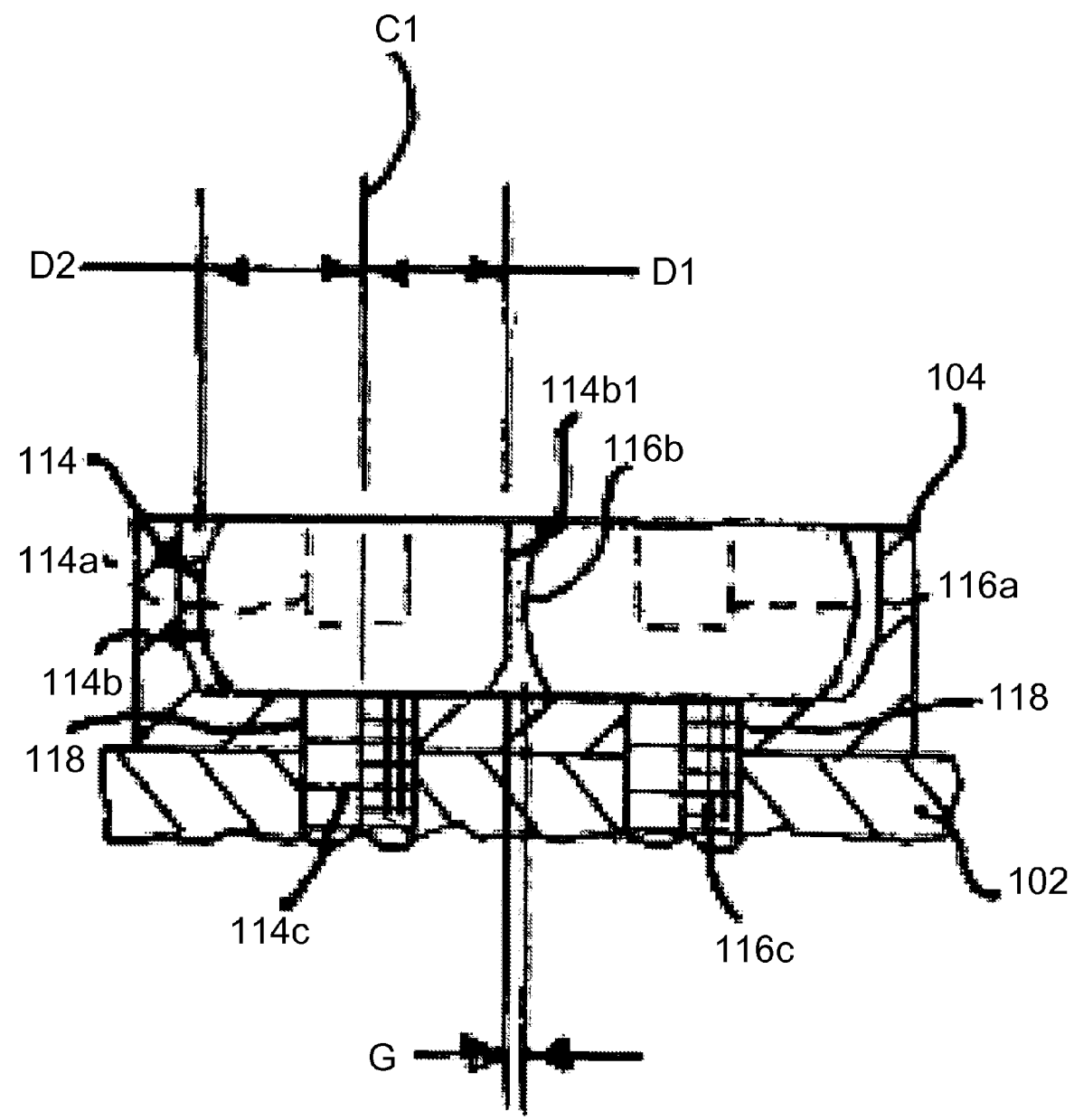
FIG. 4 is a view taken along the line A-A in FIG. 2.
Figure 5:
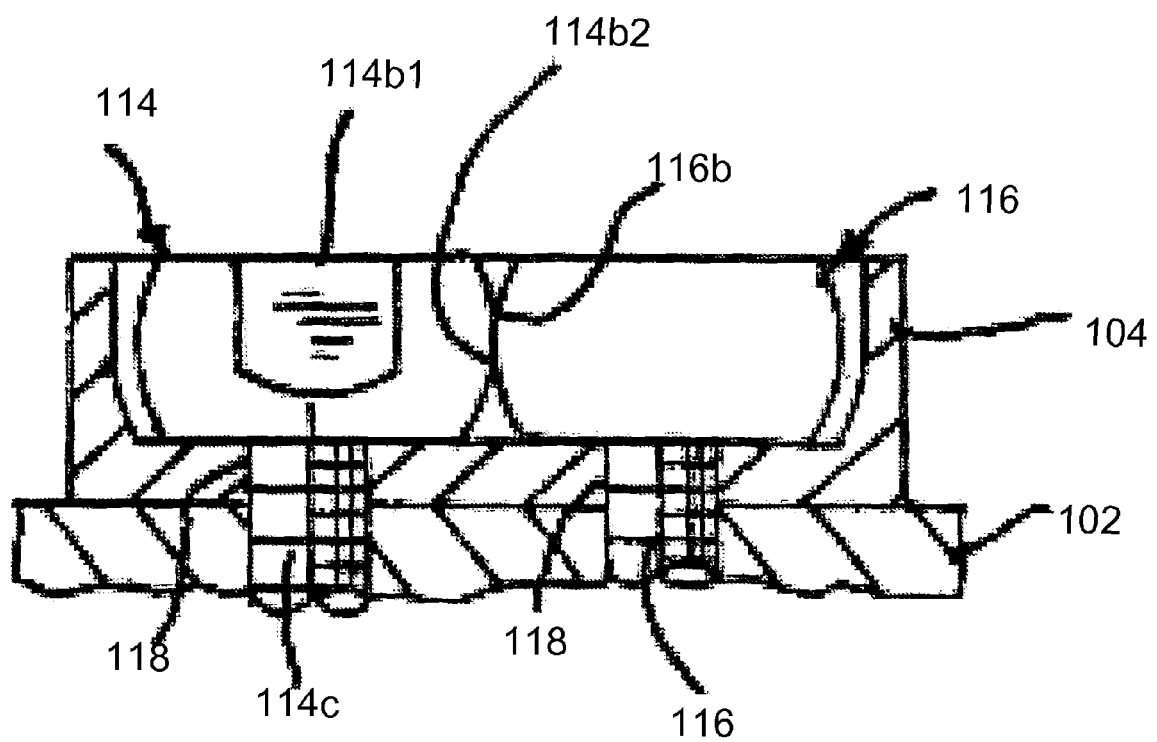
FIG. 5 is a view taken along the line B-B in FIG. 3.

The fasteners 110 and 114 comprise a head 110b and 114b that have a planar or flat portion 110b and 114b1 as shown. As best illustrated in FIGS. 4 and 5, note that the fasteners 114 and 116 each comprise threads or a threaded portion, such as threads or portions 114c and 116c of fasteners 114 and 116, respectively. Note that a distance or small radius D1 between center C1 and edge, 114b1 in FIG. 4 is smaller than the distance or large radius D2 measured by the distance between center C1 and edge 114b1 in FIG. 4. The difference in the distances D1 and D2 facilitates defining a cam surface or lobe on the wall 114b2 (FIG. 5) whose use and purpose will be defined later herein.

In the embodiment being described, one or more of the heads 110b, 112b, 114b and 116b may comprise an indicia, such as a grind mark or other indicator 120 and 122 (FIG. 2), to facilitate and assist a user, such as a doctor, to identify the small radius portion D1 during a surgical procedure. Thus, the indicia 120 and 122 facilitate defining the surface associated with the flat portion, such as portion 110b1.

Figure 3:
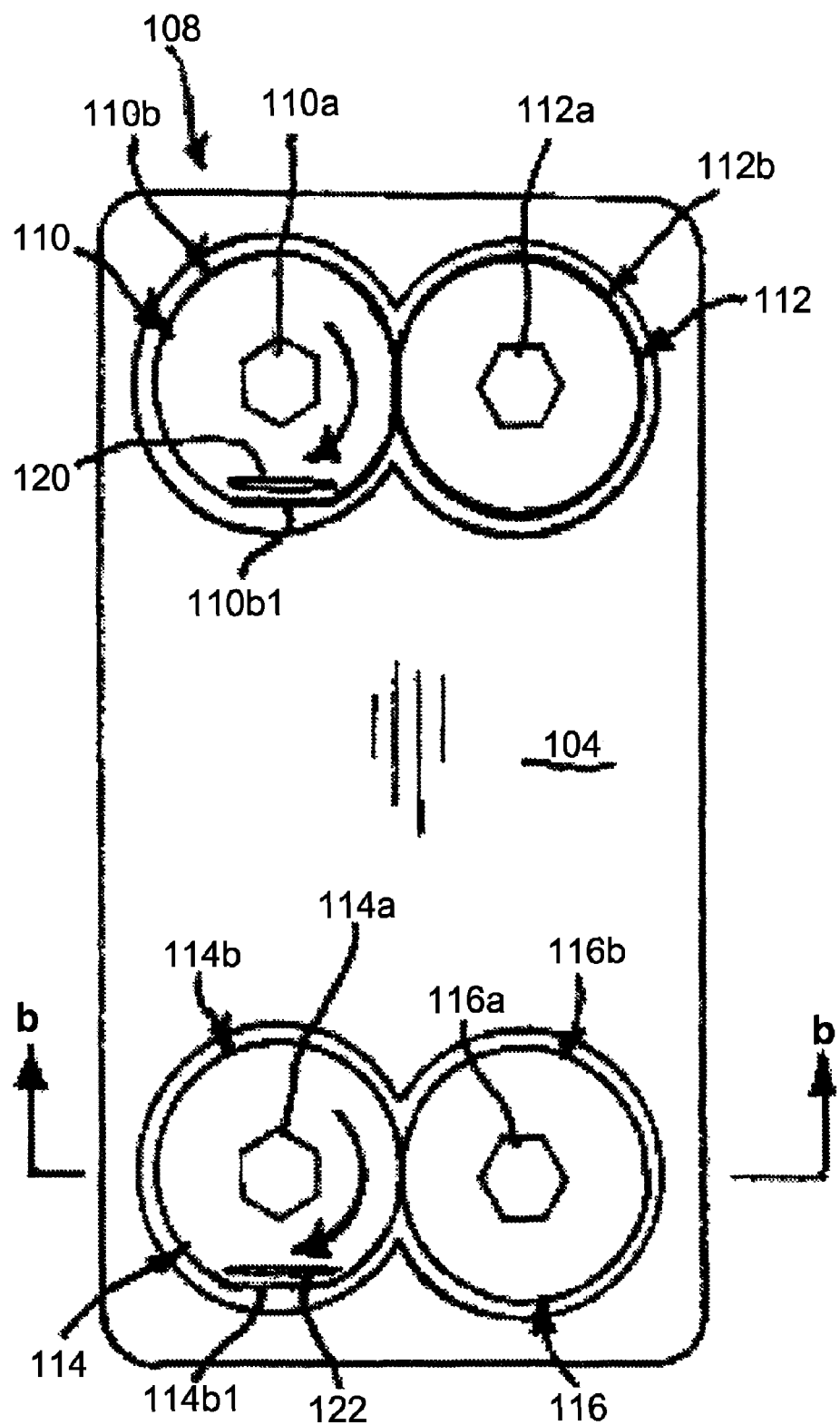
FIG. 3 is a view of the fasteners or screws shown in FIG. 2 in a locked position.

It should be understood that when the pairs of fasteners 110-112 and 114-116 are aligned such that the surfaces 110b1 and 114b1 and short or small radius portion D1 are situated in opposite or closest to wall 112b of screw 112 and wall 116b of screw 116 the adjacent fasteners 112 and 116 respectively, may be rotated and screwed into, for example, a plate 104 and a vertebrae 102 (as shown in FIGS. 4 and 5), to retain the plate 104 to the vertebrae 102. Although not shown, the locking system of the present invention may comprise eccentric fasteners of screws having eccentric heads (i.e. where a head center is offset from a thread axis) and fasteners that are used with non-eccentric fasteners. For example, and as illustrated in FIG. 3, fasteners 110 and 114 may comprise the aforementioned eccentric, while adjacent fasteners 112 and 116, respectively, may be non-eccentric fasteners or screws.

In any event, the small radius portion D1 permits the adjacent fastener or screw such as screw 116, whether it has an eccentric or not, to be turned when the small radius portion D1 or flat portion 114b1 is situated in opposed relationship to the adjacent screw (as illustrated in FIGS. 2 and 4). For example, FIG. 4 illustrates that when the fasteners are aligned such that the indicia 122 are aligned as illustrated in FIG. 2, a gap G exists between the portions 114d1 and wall 116d of screw 116 as shown. The gap G permits either or both of the fasteners 114 and 116 to rotate in either a counter-clockwise or clockwise direction during fastening and unfastening of the fasteners to the vertebrae as described earlier herein with the prior embodiments.

Figure 6:
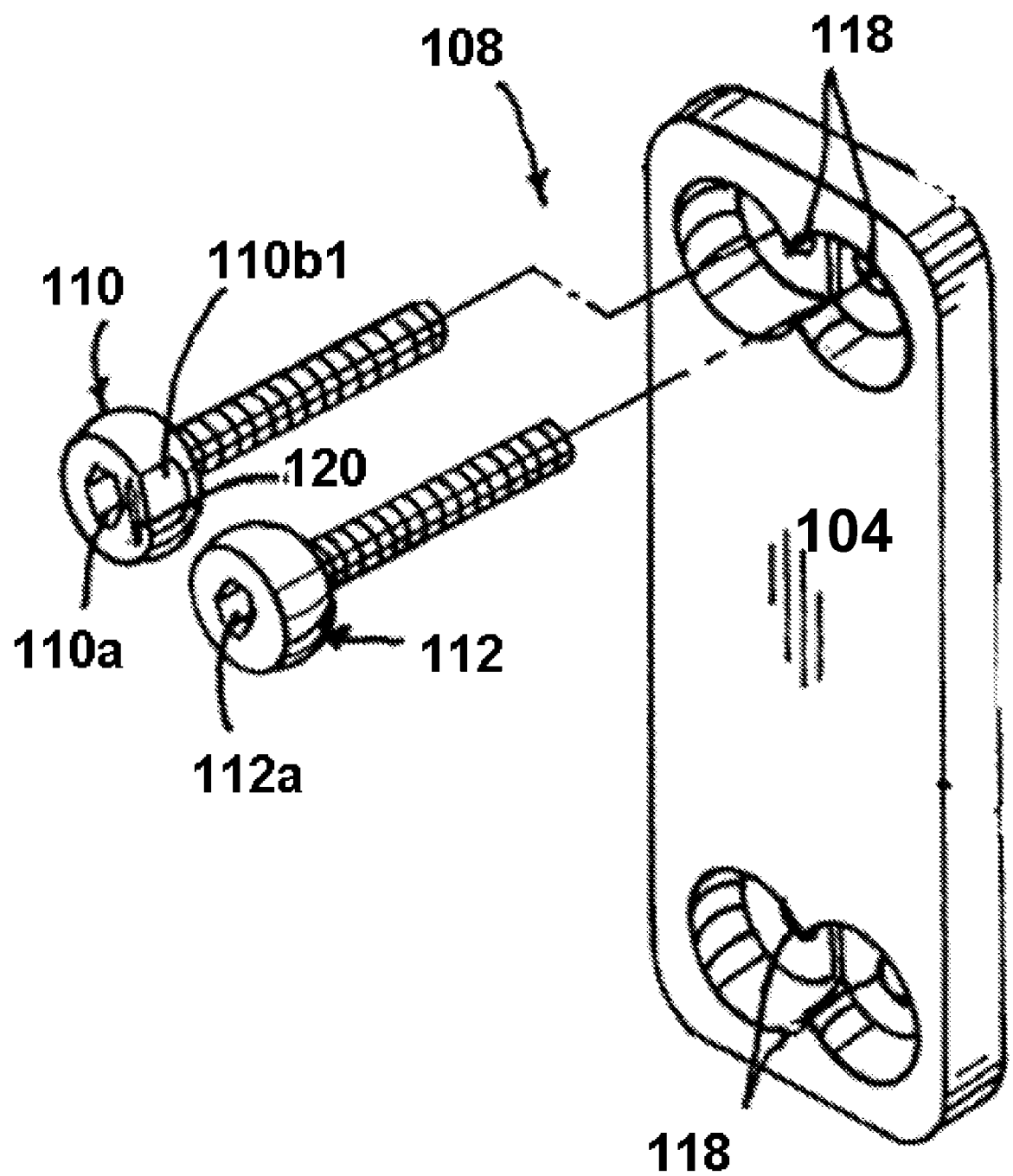
FIG. 6 is an exploded view of one embodiment with the locking screws illustrated in FIGS. 2-5.

FIG. 6 is an exploded view showing the orientation and alignment of the plate 104 and fasteners 110-116. When it is desired to secure the plate 104 to bony structures, such as vertebrae (not shown), the fasteners 110-114 are placed in the opening 118 of the plate 104. The fasteners 110-114 are then aligned as illustrated in FIG. 2. The fasteners 110-114 are rotated and screwed into vertebrae (not shown) in a clockwise direction until it is seated. These fasteners 110 and 114 are then "backed out" less than a full turn until flat surface 110b1 and 114b1 are aligned as shown in FIG. 2. The surgeon may use the indicator 120 and 122 to perform this alignment. This alignment presents the gap G (FIG. 4), which permits the fastener 116 to be rotated in a clockwise direction until completely screwed into vertebrae (not shown).

Next, the adjacent fastener (112 for the 110-112 pair and 116 for the 114-116 pair) is inserted into opening 118 in plate 104 (as shown in FIGS. 2 and 4) until they are fully seated into the vertebrae (FIGS. 4 and 5). For example, in the illustration shown in FIGS. 2 and 4, the fastener 114 is rotated in a clockwise direction with a tool, such a hex wrench (not shown) until it is fully seated into the vertebrae (not shown). The fastener 114 is again rotated in the clockwise direction (as viewed) until the large radius portion D2 and the wall portion 114b2 engages and comes against the wall 116b of the fastener 116.

It should be appreciated that when the fasteners 110-116 are secured in the locked position in the manner described, they facilitate retaining themselves in the locked position. For example, if fastener 116 begins to rotate in a counterclockwise direction (as viewed in FIG. 3) it will cause fastener 114 to rotate in a clockwise direction which, in turn, causes fastener 114 to tighten and resist the counterclockwise rotation of fastener 116. If fastener 116 would rotate, fastener 114 would screw deeper into the vertebrae 106.

While the apparatus and method described constitute preferred embodiments of this invention, it is to be understood that the invention is not limited to this precise apparatus and method, and that changes may be made in either without departing from the scope of the invention, which is defined in the appended claims.

Many similar embodiments are possible, for instance there may be:

1. a medical screw for use in association with a medical implant in a patient; said medical screw comprising, a threaded portion; and a head integral with said threaded portion, said head having a first portion permitting an adjacent screw to be screwed and an engaging portion for engaging said adjacent screw when said head portion is rotated, thereby facilitating preventing said medical screw and said adjacent screw from unscrewing.

2. The medical screw as recited in embodiment 1 wherein said head comprises: a large radius portion and a small radius portion; said small radius portion defining said first portion and permitting said adjacent screw to be turned when said small radius portion is situated in opposed relationship to said adjacent screw.

3. The medical screw as recited in embodiment 1 wherein said medical screw is titanium.

4. A locking screw for use in a prosthetic implant procedure, comprising: a threaded portion; a head portion integral with said threaded portion; and said head portion comprising a non-camming area and a camming area.

5. The locking screw as recited in embodiment 4 wherein said head portion comprises indicia associated with said non-camming area.

6. A prosthetic implant plate system comprising: a plate member; and a lock system for preventing withdrawal of at least one screw after said at least one screw is received in an opening in the plate member and screwed into a spinal bone.

7. The prosthetic implant plate system as recited in embodiment 6 wherein said lock system comprises an elongated resilient member integrally formed in said plate member; said resilient member retaining said at least one screw in a secured position in said spinal column.

8. The prosthetic implant plate system as recited in embodiment 6 wherein said resilient member is biased radially towards a head of said at least one screw such that a portion of said resilient member becomes situated over a head of said at least one screw 9. The prosthetic implant plate system as recited in embodiment 6 wherein said plate member is titanium.

10. The prosthetic implant plate system as recited in embodiment 6, wherein said lock system comprises: at least one pair of screws situated adjacent each other; at least one of said at least one pair of adjacent screws comprising a camming head for engaging a head of the other of said at least one pair of screws to facilitate retaining said screws in a tightened position.

11. The prosthetic implant plate system as recited in embodiment 10, wherein said camming head comprises a camming surface that engages said head and a non-camming surface; said non-camming surface not engaging the adjacent screw when said adjacent screw is screwed into said spinal bone.

12. The prosthetic implant plate system as recited in embodiment 10 wherein said camming head comprises a large radius portion and a small radius portion; said small radius portion permitting the other said at least one pair of screws to be screwed when said small radius portion is situated in opposed relationship to said other of said adjacent screws.

13. The prosthetic implant plate system as recited in embodiment 6, wherein said lock system comprises: a first screw and a second screw, at least one of said first screw and second screw comprising a head having a wall surface for engaging a head of the other of at least one of said adjacent screws after said screws are received in an opening in said plate member and screwed into said spinal bone.

14. The prosthetic implant plate system as recited in embodiment 11, wherein said head of at least one of said first screw or said second screw comprises an eccentric.

15. The prosthetic implant plate system as recited in embodiment 11, wherein a head said first screw comprises a head having a side wall at least a portion of which is generally flat to permit said second screw to rotate during tightening and a non-flat portion for engaging a head of said second screw to facilitate preventing untightening 16. The prosthetic implant plate system as recited in embodiment 11 wherein said first and second screws are titanium.

17. The prosthetic implant plate system as recited in embodiment 11 wherein said camming head comprises an indicator associated with said non-camming surface.

18. A locking system for retaining a prosthetic implant to a vertebrae comprising: a first fastener for retaining securing said prosthetic implant cover on to said vertebrae; and at least one second fastener that for securing said prosthetic implant to said vertebrae; said at least one second fastener engaging engages said first fastener to retain at least one of said first fastener or said at least one and second fasteners thereto fastener in a tightened position.

19. The locking system as recited in embodiment 18 wherein said at least one second fastener comprises a head having an eccentric for engaging said first fastener.

20. The locking system as recited in embodiment 18 wherein said first fastener and said at least one second fastener each comprise a generally flat portion and an eccentric portion.

21. The locking system as recited in embodiment 19 wherein said at least one second fastener comprises an indicia to identify said generally flat portion.

22. The medical screw as recited in embodiment 1 wherein said head comprises an eccentric 23. The locking screw as recited in embodiment 4 wherein said non-camming area comprises either a flat area or a small radius area 24. The medical screw as recited in embodiment 1 wherein said head comprises an eccentric.

25. The locking screw as recited in embodiment 4 wherein said head portion comprises indicia to identify said non-camming area.

26. The locking system as recited in embodiment 18 wherein said first fastener comprises an eccentric head.

27. The locking system as recited in embodiment 26 wherein said eccentric head has a small radius portion associated with said flat portion.

28. The locking system as recited in embodiment 18, wherein said first fastener comprises a flat portion.

29. The locking system as recited in embodiment 18, wherein said at least one fastener comprises an eccentric head.

30. A locking screw for use with a prosthetic implant plate, comprising: a threaded portion; and a head portion integral with said threaded portion; said head portion comprising a non-camming area for permitting an adjacent screw to be screwed and engaging portion for engaging said adjacent screw when said locking screw and said adjacent screw are screwed into a spinal bone to facilitate retaining said locking screw and said adjacent screw in a tightened position.

31. A plate system for mounting on a spinal column, said plate system comprising: a plate having a plurality of openings; and a plurality of screws for receipt in said plurality of openings, respectively, and screwed into a spinal bone of said spinal column; said plurality of screws having heads that engage to retain said plurality of screws in a tightened position.

32. The plate system as recited in embodiment 31 wherein said plurality of screws comprise: a first screw having a first head, said first head comprising a wall having a first portion and a second portion; and a second screw having a second head having a second wall; said first portion being dimensioned such that when said first portion is situated opposite said second wall, said second head may be rotated to screw said second screw into said spinal bone of said spinal column, said first portion of said first screw may thereafter be rotated so that said second portion may engage said second wall in order to facilitate retaining said first and second screws in a tightened position.

33. The plate system as recited in embodiment 32 wherein said first screw comprises an eccentric defining both said first portion and said second portion.

34. The plate system as recited in embodiment 32 wherein said first portion comprises a generally flat area.

35. The plate system as recited in embodiment 32 wherein said first portion comprises a small radius portion and said second portion defines a second radius portion that is larger than said small radius portion.

37. The plate system as recited in embodiment 31 wherein said plurality of screws comprises: a first screw having a first head; and a second screw having a second head; said first head having a wall having a first portion that is dimensioned to permit said second head to rotate and a second portion dimensioned to engage said second head when said first screw is rotated to facilitate preventing said first and second screws from backing out.

38. The plate system as recited in embodiment 37 wherein said first portion comprises a generally flat area.

39. The plate system as recited in embodiment 37 wherein said first portion comprises a first radius portion and said second portion defines a second radius portion that is larger than said first radius portion.

40. The plate system as recited in embodiment 31 wherein at least one of said first screw or said second screw comprises an eccentric.

41. The plate system as recited in embodiment 37 wherein said plurality of screws comprises: a third screw having a third head; and a fourth screw having a fourth head; said third head having a wall having a portion that is dimensioned to permit said fourth head to rotate and a second portion dimensioned to engage said fourth head when said third screw is rotated to facilitate preventing said third and fourth screws from backing out.

42. A method for fastening a plate to a spinal column comprising the steps of: situating the plate in proximity to the spinal column; positioning a first screw through an aperture in the plate; screwing said first screw into a spinal bone in the spinal column; positioning a second screw through the plate; screwing a second screw into the spinal bone until it becomes tightened; and tightening said first screw until a portion of a head of the first screw engages a head of the second screw to retain the first and second screws in a tightened position.

43. The method as recited in embodiment 42 wherein said first screwing step comprises the step of: backing out said first screw less than a full turn before said second screwing step.

44. The method as recited in embodiment 42 wherein said first screwing step comprises the step of: backing out said first screw less than a full turn until a portion of a head of said first screw becomes situated opposed to a head of the second screw.

45. The method as recited in embodiment 42 wherein said first screwing step comprises the step of: using an indicia on said head of said first screw to perform said backing out step.

46. The method as recited in embodiment 42 wherein said first screw comprises a cam head.

47. The medical screw as recited in embodiment 1 wherein said head comprises an indicator to identify said first portion.

What is claimed is:

1. A plate system for mounting on a spinal column, said plate system comprising:
   a plate having a plurality of openings; and a plurality of screws for receipt in said plurality of openings, respectively, and screwed into a spinal bone of said spinal column; said plurality of screws having heads that engage to retain said plurality of screws in a tightened position;
   each of said plurality of screws having a threaded portion monolithically formed with a head, a head of at least one of said plurality of screws being situated adjacent to an adjacent one of said plurality of screws after said at least one of said plurality of screws and said adjacent one of said plurality of screws are received in said plate, said head of said at least one of said plurality of screws comprises a first portion sized and shaped to permit said adjacent one of said plurality of screws to be screwed into bone and after it is screwed into bone, said at least one of said plurality of screws can be screwed into bone so that a second portion of said head of said at least one of said plurality of screws engages a head of said adjacent one of said plurality of screws to retain said plurality of screws in said tightened position;
   wherein said first portion comprises a first radius and said second portion comprises a second radius that is larger than said first radius.

2. The plate system as recited in claim 1 wherein said plurality of screws comprises:
   a first screw having a first head; and
   a second screw having a second head;
   said first head having a side or radial wall defining said first portion that is dimensioned to permit said second head to rotate and said second portion dimensioned to engage a side or radial wall of said second head when said first screw is rotated to facilitate preventing said first and second screws from backing out.

3. The plate system as recited in claim 2 wherein said first portion comprises a generally flat area.

4. The plate system as recited in claim 1 wherein said head of said at least one of said plurality of screws comprises an eccentric.

5. The plate system as recited in claim 1 wherein said plurality of screws comprise:
   a first screw having a first head, said first head comprising a wall having said first portion and said second portion; and
   a second screw having a second head having a second wall;
   said first portion being dimensioned such that when said first portion is situated opposite said second wall, said second head may be rotated to screw said second screw into said spinal bone of said spinal column, said first portion of said first screw may thereafter be rotated so that said second portion may engage said second wall in order to facilitate retaining said first and second screws in the tightened position, said second portion having a radius of curvature that is larger than a radius of curvature of said first portion.

6. The plate system as recited in claim 5 wherein said first head of said first screw comprises an eccentric defining both said first portion and said second portion.

7. The plate system as recited in claim 5 wherein said first portion comprises a generally flat area.

8. The plate system as recited in claim 5 wherein said first portion comprises a small radius portion and said second portion defines a second radius portion that is larger than said small radius portion.

9. The plate system as recited in claim 2 wherein said plurality of screws comprises:
   a third screw having a third head; and
   a fourth screw having a fourth head;
   said third head having a wall having a portion that is dimensioned to permit said fourth head to rotate and a second portion dimensioned to engage said fourth head when said third screw is rotated to facilitate preventing said third and fourth screws from backing out.

* * * * *

UNITED STATES PATENT AND TRADEMARK OFFICE
CERTIFICATE OF CORRECTION

Page 1 of 1

PATENT NO. : 8,062,367 B2
APPLICATION NO. : 11/622487
DATED : November 22, 2011
INVENTOR(S) : David Louis Kirschman It is certified that error appears in the above-identified patent and that said Letters Patent is hereby corrected as shown below:

On the Title Page, Item (63), Related U.S. Application Data, please delete "11/858,629" and insert -- 10/858,629 -- therefor.

On Title Page 2, Item (56), Foreign Patent Documents, the following foreign reference was left out of the printing of the patent: please add -- GB 0401362.9 DePuy International --.

In Column 1, Line 34, after vertebrae, please insert -- to --.

In Column 1, Line 49, after This, please delete "is".

In Column 3, Line 5, please delete "110b" and insert -- 110b1 -- therefor.

In Column 5, Line 33, after untightening, please insert -- . --.

In Column 5, Line 59, after eccentric, please insert -- . --.

In Column 5, Line 62, after area, please insert -- . --.

Signed and Sealed this
Fourth Day of December, 2012

David J. Kappos
*Director of the United States Patent and Trademark Office*